(12) United States Patent
Mueller

(10) Patent No.: US 6,611,540 B1
(45) Date of Patent: Aug. 26, 2003

(54) DIODE-LASER SYSTEM FOR HYPERPOLARIZED HE-3 AND XE-129 GAS GENERATION AND OTHER APPLICATIONS

(76) Inventor: Otward Maria Mueller, 96 Sweet Rd., Ballston Lake, NY (US) 12019-1804

( * ) Notice: Subject to any disclaimer, the term of this patent is extended or adjusted under 35 U.S.C. 154(b) by 0 days.

(21) Appl. No.: 09/363,479

(22) Filed: Jul. 29, 1999

(51) Int. Cl.[7] .............................................. H01S 3/045
(52) U.S. Cl. .......................................... 372/35; 372/36
(58) Field of Search ............................... 372/34, 35, 36

(56) References Cited

U.S. PATENT DOCUMENTS

| | | |
|---|---|---|
| 4,580,268 A | 4/1986 | Barr |
| 4,719,631 A | 1/1988 | Conaway |
| 4,912,715 A | 3/1990 | Aoki |
| 5,105,429 A | 4/1992 | Mundinger et al. |
| 5,247,183 A | 9/1993 | Tocci |
| 5,274,653 A | 12/1993 | Ohashi |
| 5,337,323 A | 8/1994 | Rokugawa |
| 5,495,490 A | 2/1996 | Rice |
| 5,545,396 A | 8/1996 | Albert et al. |
| 5,617,860 A | 4/1997 | Chupp et al. |
| 5,628,196 A | 5/1997 | Farmer |
| 5,764,675 A | 6/1998 | Juhala |
| 5,860,295 A | 1/1999 | Cates et al. |

2002/0110165 A1 * 8/2002 Filgas ........................... 372/36

\* cited by examiner

*Primary Examiner*—Leon Scott, Jr.
(74) *Attorney, Agent, or Firm*—Leonard Cooper

(57) ABSTRACT

Commercially available diode lasers are operated immersed in liquid nitrogen (LN2, 77 K), in another cryo-fluid, or are cryo-cooled (77 K–250 K) by conduction in all high-power (>0.1 W) applications. The result is higher output power per diode chip area, higher conversion efficiency, lower cost per watt of laser power, longer lifetime, higher reliability, smaller thermal gradients inside the laser chip and therefore better thermal management due to the higher thermal conductivity of the semiconductor and substrate material. The cryo-diode lasers are driven by cryogenically cooled and integrated power electronics ciruitry using Cryo-MOSFETs or Cryo-CMOS ICs. Applications of the Cryo-Diode Laser/Cryo-Driver assembly include generation of hyperpolarized He-3 or Xe-129 gases for inert gas magnetic resonance imaging of the airways in human beings, metal and materials working and processing with laser tools, "pumping" solid-state lasers and many others. In high-power laser applications, the invention makes use of the "load shedding" capability of liquid nitrogen. The Cryo-Diode Laser/Cryo-Driver assembly can also be supplied with cooling fluid from an LN2 distribution system provided by a HTS cable. MLI is used for energy storage in laser pulse power applications.

18 Claims, 11 Drawing Sheets

Schematic of Hyper-Polarized $^{129}$Xe and $^{3}$He Production System using Cryo-Diode Lasers (CDLs).

Light Output vs LED-Current

LED Light Output as a Function of Diode Current
4 x HLMA-CL00 Yellow HP Diodes [39]

Light Output for Laser Diodes: 77 K, 300 K

THERMAL CONDUCTIVITY VS TEMPERATURE, K
SILICON, GERMANIUM, GALLIUM-ARSENIDE

THERMAL CONDUCTIVITY VS TEMPERATURE FOR CU, BE and BEO

Frequency Dependence of TC4422 Driver Current at Temperatures of 300 K and 77 K for Load Capacitances of 7.5 nF and 0 nF Schematic of Hyper-Polarized $^{129}$Xe and $^3$He
Production System
using Cryo-Diode Lasers (CDLs).

DIODE-LASER SYSTEM FOR HYPERPOLARIZED HE-3 AND XE-129 GAS GENERATION AND OTHER APPLICATIONS

BACKGROUND

1. Field of Invention

This invention relates to the generation of low-cost, high-efficiency, high-power laser light for many applications using semiconductor diode lasers combined with their driver circuitry, both of which are immersed in a cryogenic cooling fluid such as liquid nitrogen (77 K) or others.

2. Discussion of Prior Art

A problem with conventional magnetic resonance proton imaging (MRI) is that airspaces such as in the lung, throat, etc. cannot be imaged [1–5]. Therefore, human pulmonary airway diseases (cystic fibrosis, etc.) could not be diagnosed by MRI in the past. But this situation is changing. The status as explained by the experts in the field [3] is as follows: "The ability to optically polarize the nuclei of the inert gases helium-3 and xenon-129 to 30% to 50% levels has made available a powerful new signal source for magnetic resonance imaging examinations. The non-equilibrium nuclear polarization of this hyperpolarized (HP) gas can be as much as $10^4$–$10^5$ times larger than the equilibrium polarization of the hydrogen protons in water used in conventional MR imaging experiments. Even though the spin density of the gases (at 1 atm) is roughly 3,000 times smaller than that of water, this still represents a substantial net gain in signal amplitude" [3]. Hyperpolarized (HP) gas is generated by light 'pumping' with semiconductor diode lasers. "Not surprisingly, the amount of gas that can be polarized is ultimately limited by the laser power that is available." [3]. The light output power of the pumping diode lasers for the generation of the hyperpolarized gases is in the order of magnitude of 10–150 watt [6]. Diode lasers are cost effective by an order of magnitude compared to Ti:sapphire lasers. But at these output levels they are nevertheless still very expensive. A 500 mW laser diode may cost as much as $200–$500 depending on quantities. Important new laser diode applications as discussed here may require 100 W at a cost of $40,000 to $80,000. Therefore, an attempt must be made to reduce their cost in order to permit a widespread introduction of this new promising hyperpolarized gas magnetic resonance imaging technique into many hospitals. Thus, one can state that prior art is expensive, inefficient, and of low power output.

In addition to the use of diode lasers for inert gas polarization and generation there are many other applications for these sources of laser light to be discussed later.

Objects and Advantages

Measurements on light-emitting diodes (LEDs) show that their light output if immersed in liquid nitrogen (LN2, 77 K) can be one to two orders of magnitude higher than at room temperature (300 K) for the same diode current. In FIGS. 1 and 2 the output for a yellow LED as a function of the diode current is plotted for 300 K and 77 K, demonstrating the increase in efficiency by cryo-cooling. From these measurements, one can conclude that GaAs laser diodes may behave in a similar fashion. This is proven for a red diode laser in FIG. 3. If by cryo-cooling the output power of a laser diode can be increased by a factor N, then the cost for a given power level is reduced by a factor N, neglecting, in a first order approximation, the cooling penalty cost.

Very high current and power densities occur in diode lasers. Improved thermal management is therefore extremely important. FIGS. 4 and 5 demonstrate how cryo-cooling drastically increases the thermal conductivity of semiconductor materials and usual substrates such as beryllium and beryllium-oxide. Therefore cryo-cooled diodes will have smaller temperature gradients, which improves the lasing action as well as the thermal management of the system. Note that according to FIG. 5, the thermal conductivity of beryllium and BeO at 77 K is higher than that of copper.

A key object of this invention is to integrate the driver circuitry with the diode laser in a cryogenic environment, such as a bath of liquid nitrogen (LN2) at 77 K. In addition to the improved performance of the semiconductor laser, one obtains all the advantages of cryo-cooled power electronics based on the use of power Cryo-MOSFETs and Cryo-COOL-MOS devices: Higher efficiency, higher speed, longer lifetime, higher reliability, smaller size, etc. [27–31]. It has been found that certain integrated CMOS circuits such as the TC4422/21 (9 A) drivers are well suited for cryogenic operation. Cryo-cooling increases their efficiency by reducing their current consumption. In addition, their switching speeds increase at low temperatures, thus decreasing their switching losses. FIG. 6 shows the reduction in driver circuit current of the TC4422 as a function of frequency for a load capacity of 0 nF and 7.5 nF at temperatures of 300 K and 77 K.

The efficiency of semiconductor diode lasers can be high (20% to 60%). Nevertheless, they generate considerable heat. A dissipation energy of 45 Wh evaporates one liter of liquid nitrogen (LN2). But one can here make use of the "load shedding" property of LN2, which can be generated in off-peak hours. For many applications where high laser power is not continuously required, the cost of liquid nitrogen may be less than that of additional laser diodes, which would be required for normal temperature (300 K) operation.

BRIEF DESCRIPTION OF THE DRAWINGS

One possible implementation of a cryo-diode laser-plus-driver system for the generation of hyperpolarized gas for magnetic resonance imaging is shown in FIG. 7. A dewar 1 contains an array of laser junction diodes 4 consisting of a suitable gallium-arsenide compound generating a laser beam of a wavelength of 795 nm for this application immersed in a liquid nitrogen (LN2) bath 2. Multilayer insulation (MLI) 3 provides good thermal isolation and low thermal losses. The new concept of cryogenic power conversion [27–31] is also applied: Cryo-MOSFETs 5 and 6 with their drivers 10 and 11 and a filter network 7, 8 and 9 act as drive circuits for the GaAs laser diode array 4. Such driver circuitry is especially required for pulsed applications. The integration of drive circuitry and laser diode permits the minimization of lead inductances between the output of the driver and the diode laser terminal. This is important for high-speed laser switching in other applications. A fiber optic cable 12 transmits the linearly-polarized diode laser light to the polarization optics 13 which transforms it into a circularly polarized laser beam which "pumps" the helium-3 or xenon-129 polarization cell and oven 14, 15. Helmholtz coils 16 generate a magnetic field for the polarization of the gas spins. The laser diodes are preferably mounted on a heatsink which is also immersed in the LN2.

Figure 1:
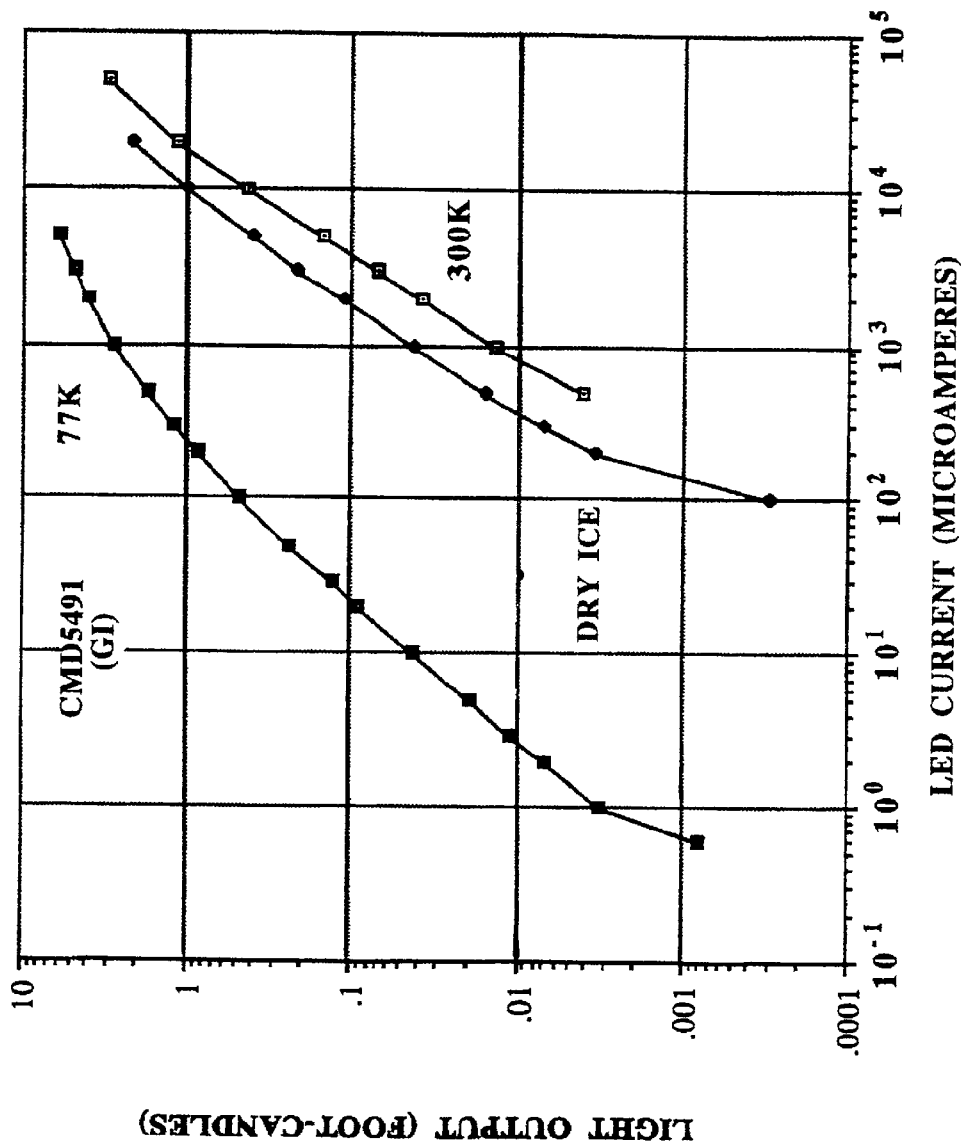
FIGS. 1–6: These have been discussed above.
Figure 2:
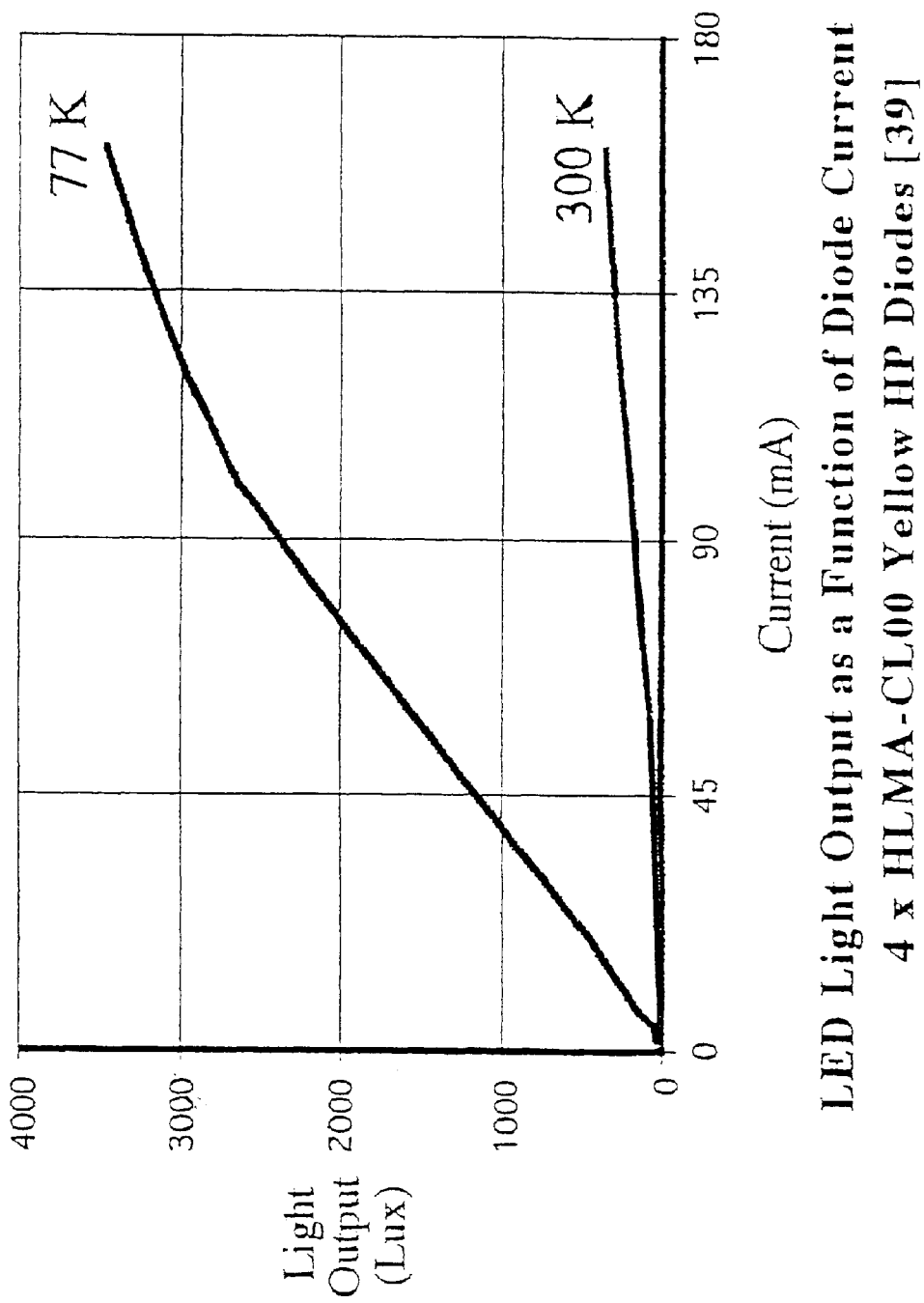
Figure 3:
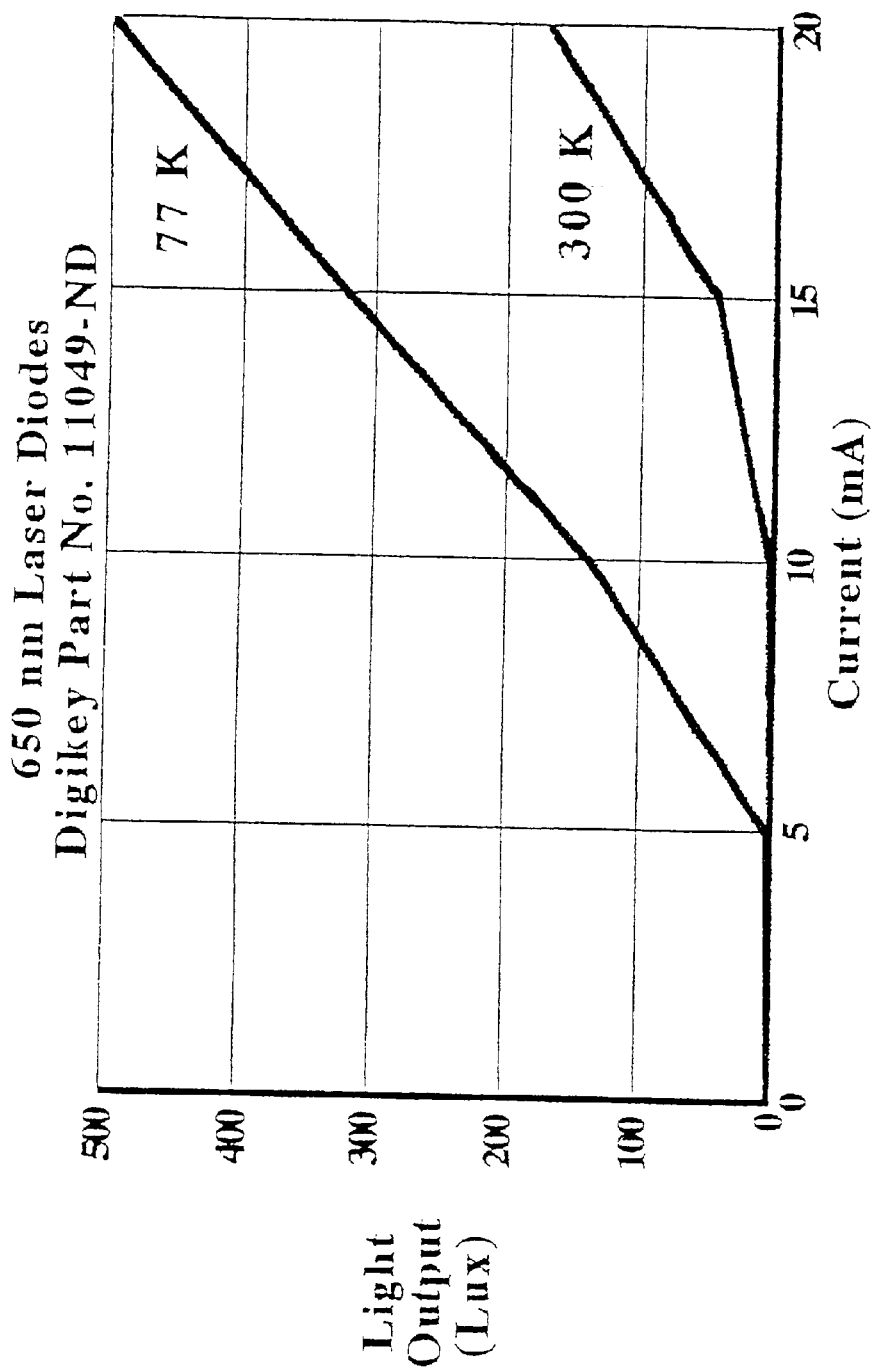
Figure 4:
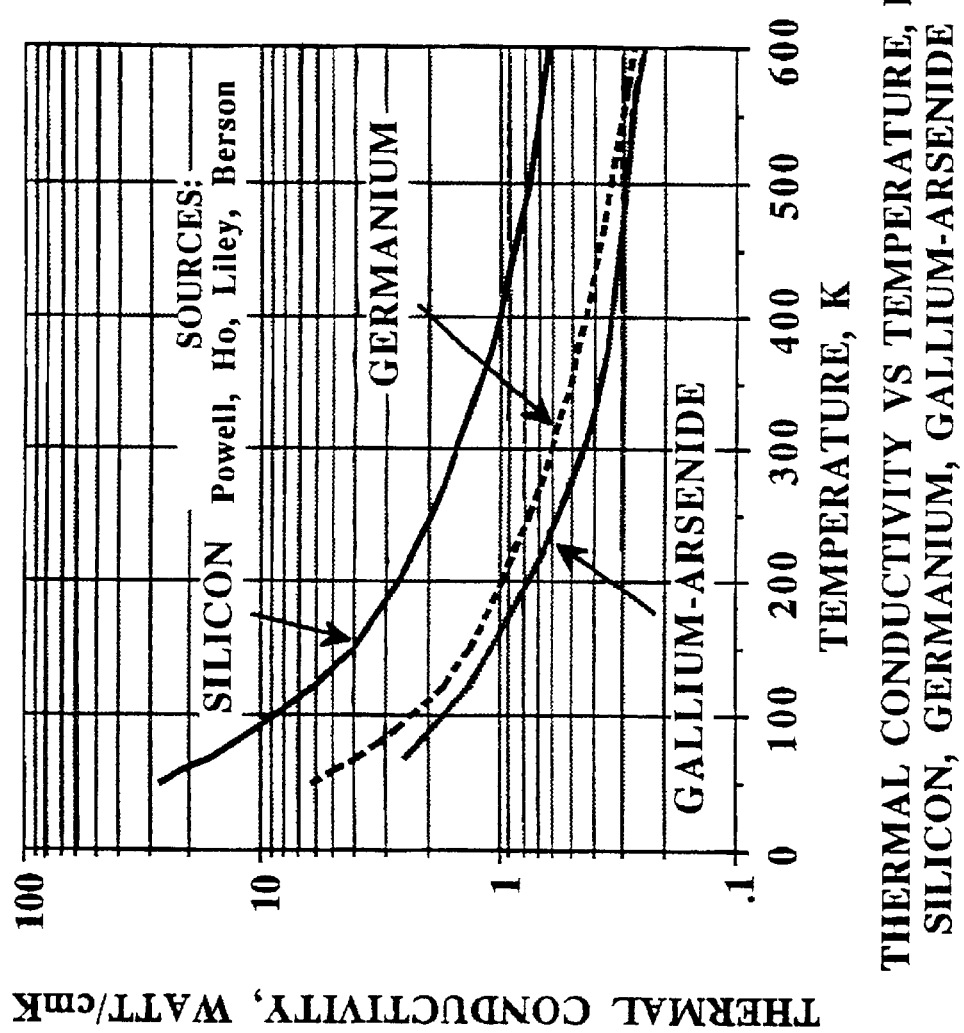
Figure 5:
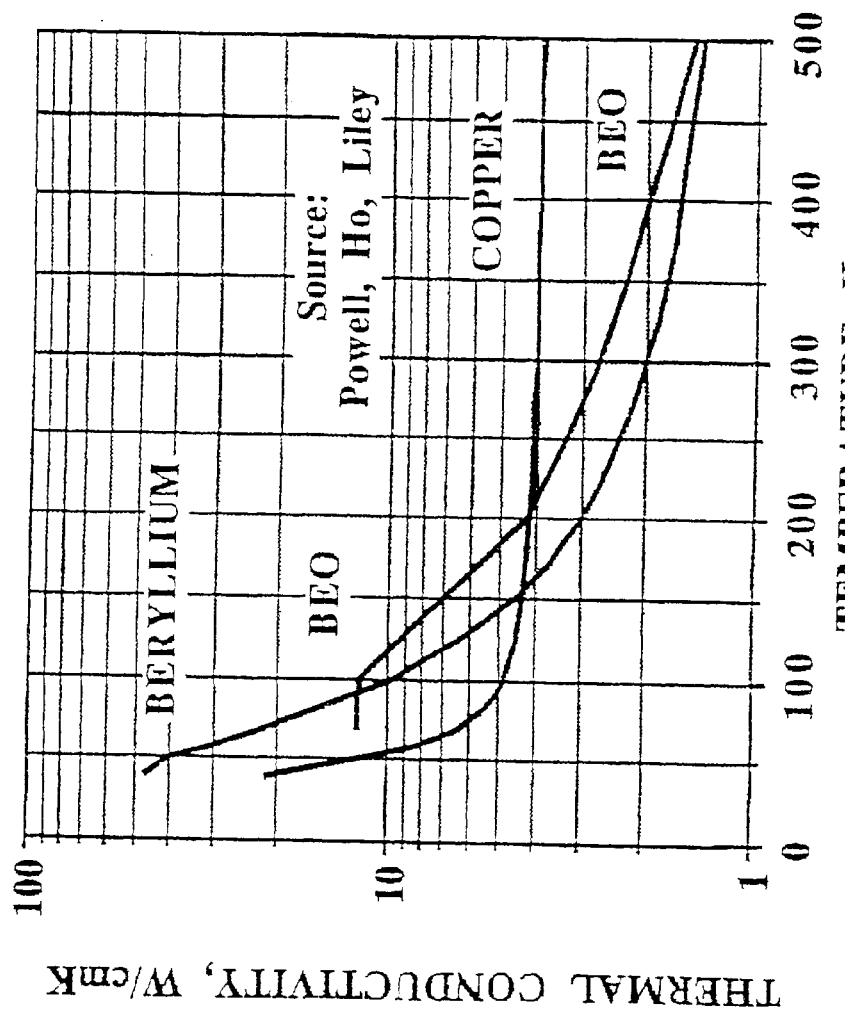
Figure 6:
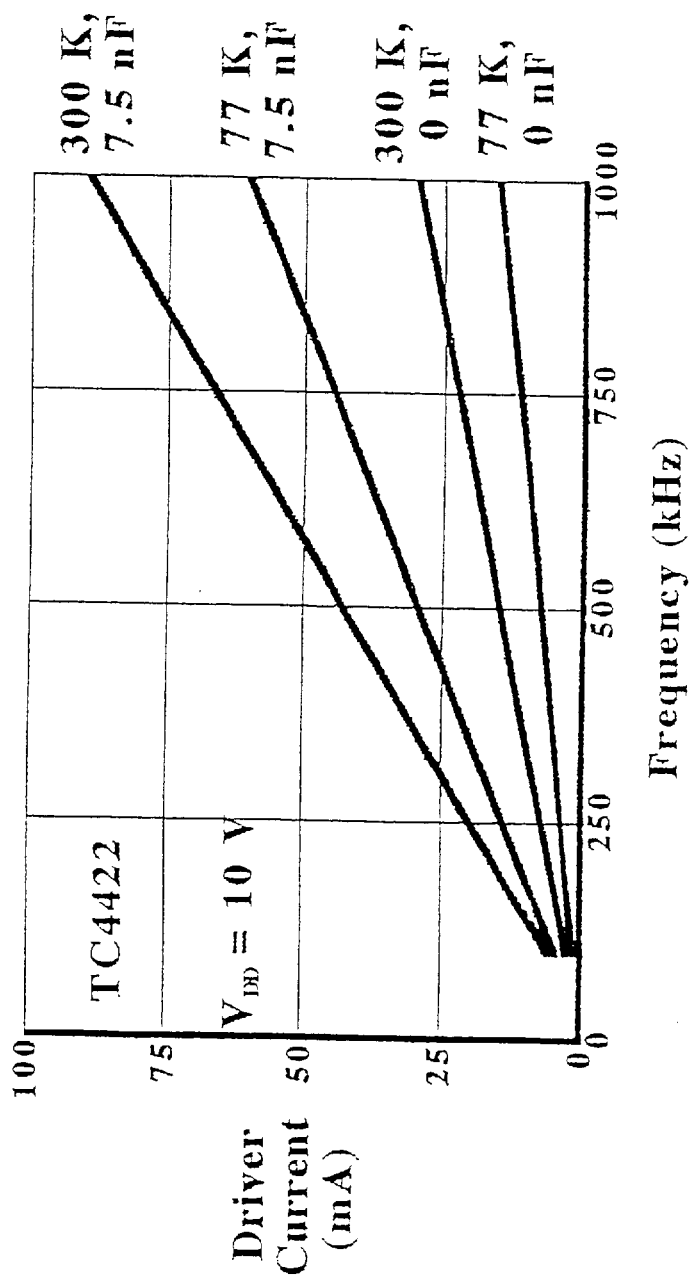

The cryo-cooled diode-laser-driver system can also be used for other applications such as for diode laser pumping of solid-state lasers. A cryogenic dewar 1 using multi-layer insulation 3 contains the diode laser assembly 4 supplied with power by driver circuitry 17. The laser diodes 4 provide the "pumping" light to the solid-state laser 22 whose properties also improve by cryo-cooling. The LN2 supply line 19 provides the cooling fluid 2 and exhaust 18 permits the release of the nitrogen vapor. Fiber optic cables 12 delivers the laser light.

Figure 8:
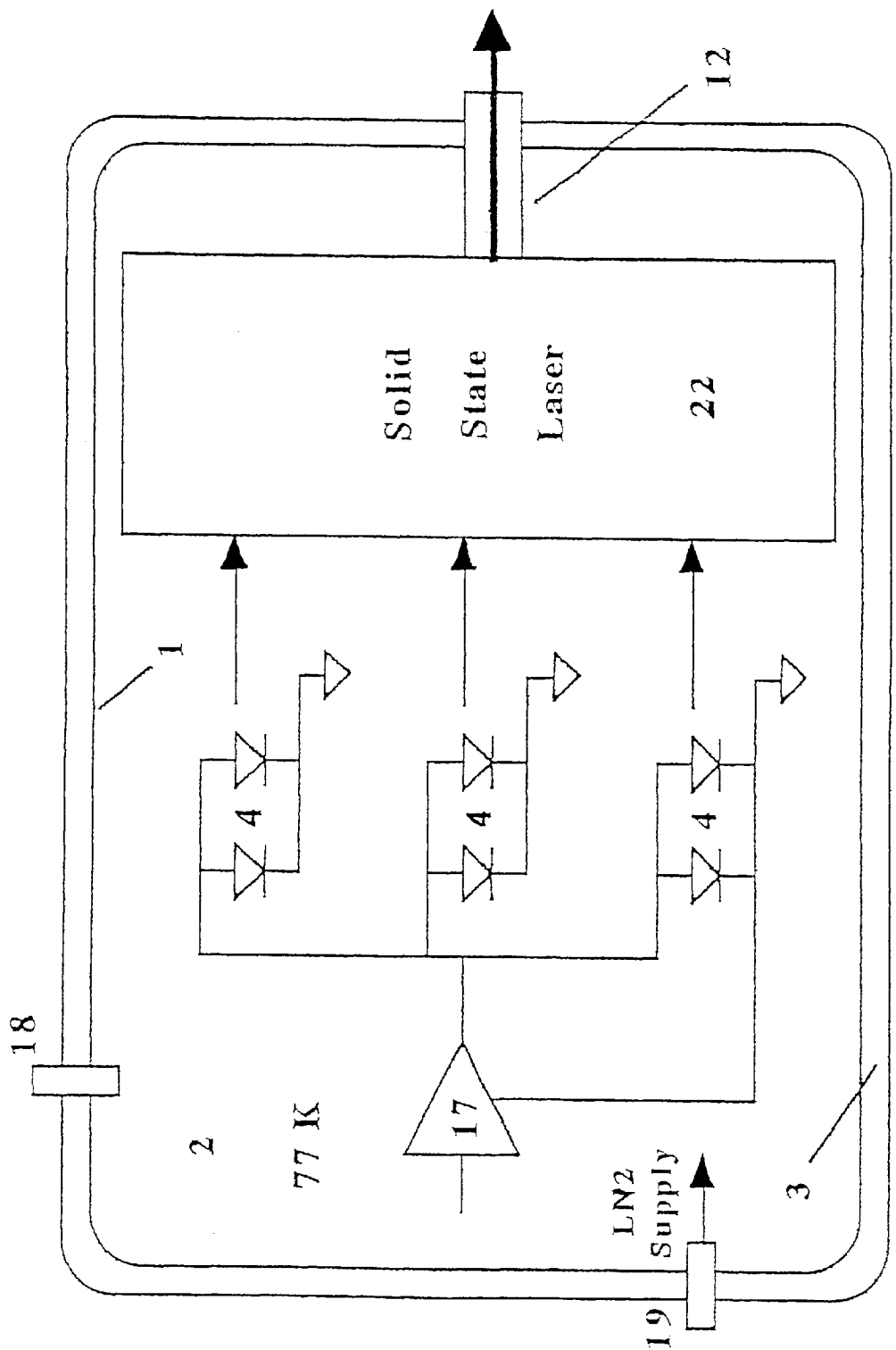
FIG. 8.
Figure 9:
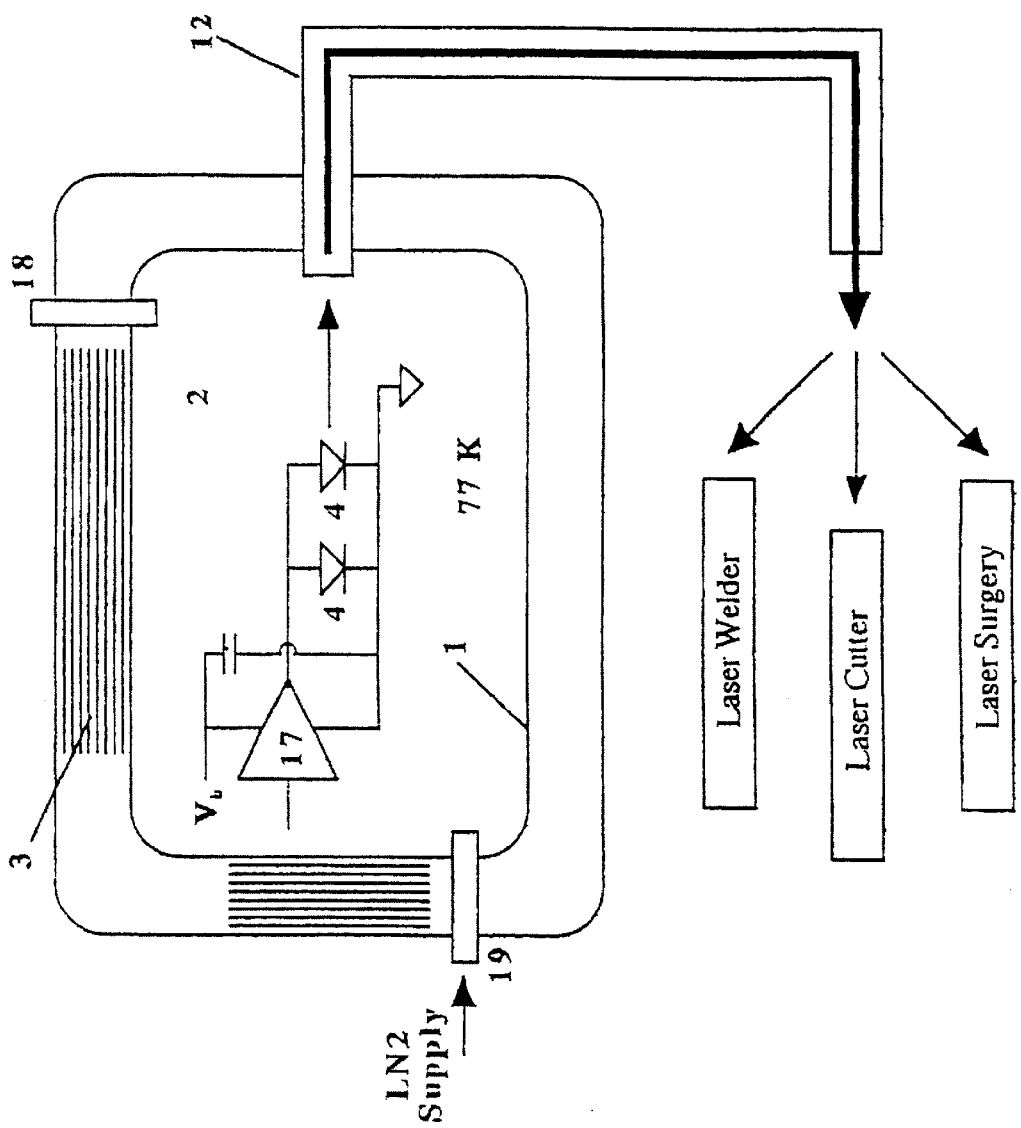
Figure 10:
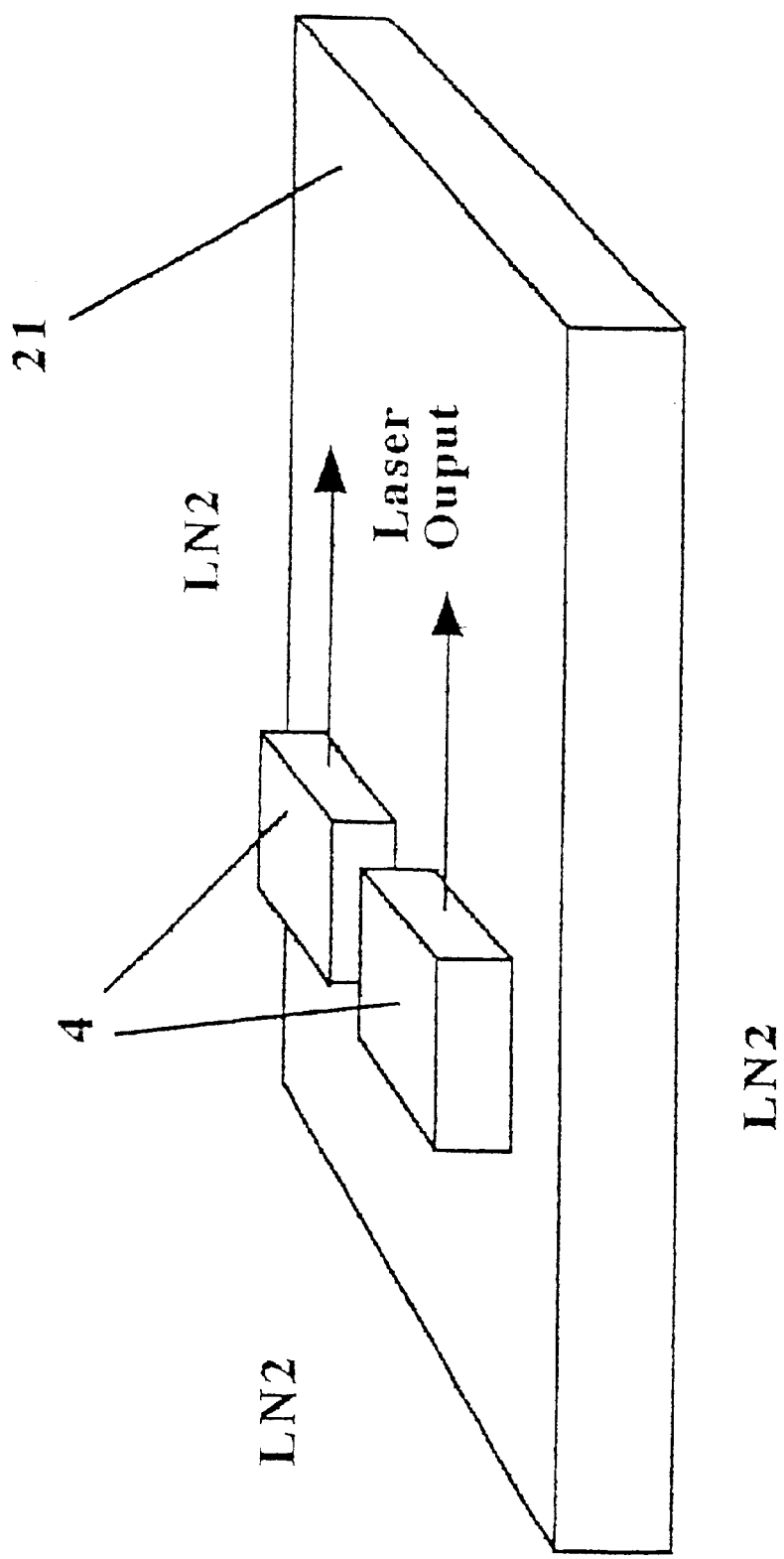
(FIG. 10). The heatsink permits fast removal of the concentrated power dissipation. An LN2 supply 19 and exhaust 18 are also provided. Of course, conduction cooling could also be applied if low-cost cryo-coolers should become available in the future.

FIG. 9:

The cryo-diode laser 4 light (or solid-state laser light of FIG. 8) can also be used for many other applications such as laser welding, laser cutting, laser surgery and many others. The multi-layer insulation (MLI) can be used to implement energy storage capacity for pulsed laser applications.

FIG. 10:

The laser diodes 4 are preferably mounted on suitable substrates 21 consisting of beryllium-oxide, diamond substrates, or others having a high thermal conductivity at low temperatures.

Figure 11:
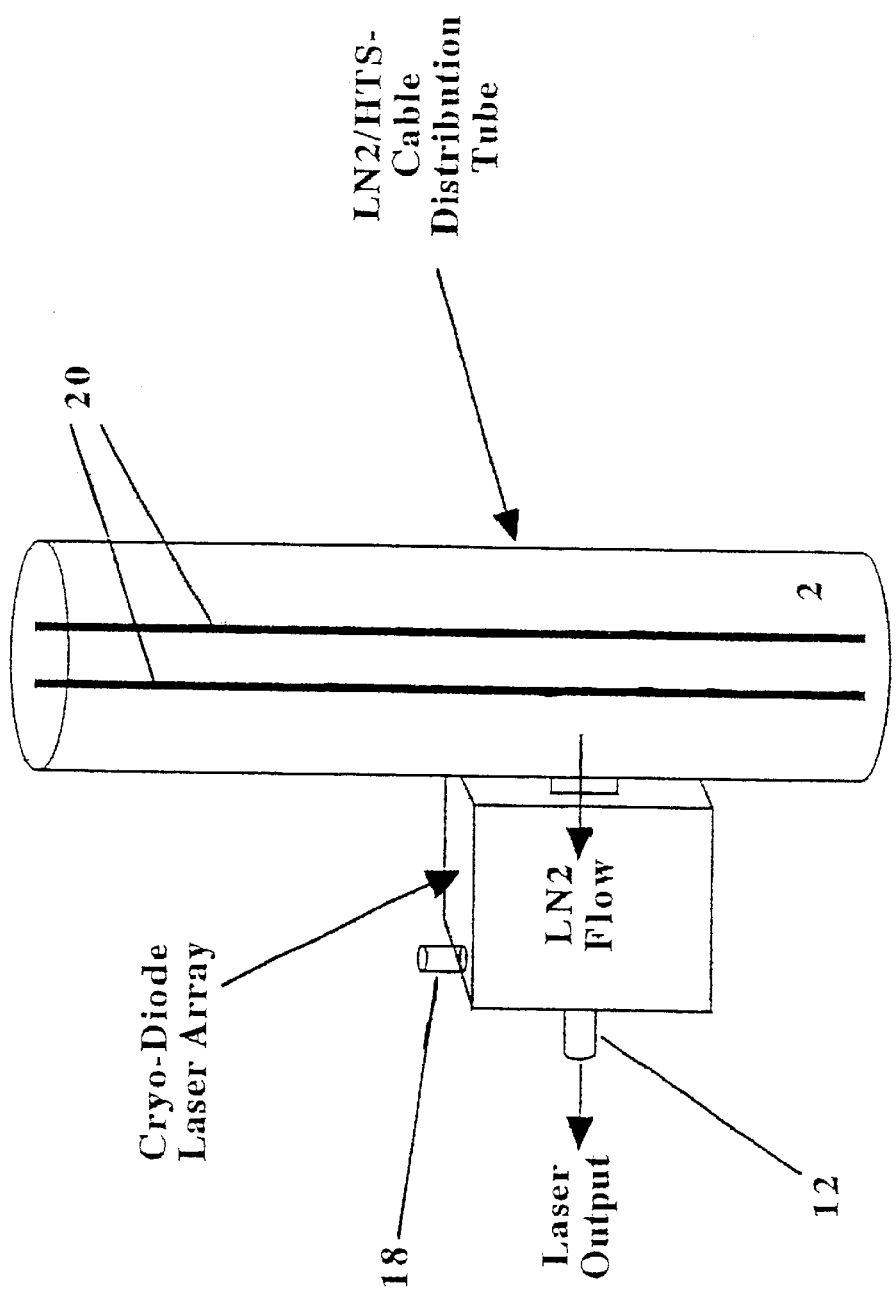

FIG. 11:

In the coming age of Cryogenics, high-temperature superconductor (HTS) cables 20 will supply electrical energy as well as the cooling fluid 2, e.g. liquid nitrogen 2 to cryogenic power circuits such as the cryo-diode laser array assembly 1. This is shown in FIG. 11 [33, 34]. In a magnetic resonance imaging (MRI) system using superconducting magnets and other cryo-cooled circuits such as gradient cryo-power amplifiers the cryo-diode laser equipment 1 for the generation of the polarized gases can also be integrated into the overall cryo-cooling system.

REFERENCE NUMERALS IN DRAWINGS

| 1 | dewar |
| 2 | liquid nitrogen |
| 3 | multi-layer insulation (MLI) |
| 4 | laser diode |
| 5 | high-side MOSFET |
| 6 | low-side MOSFET |
| 7 | inductor |
| 8 | capacitor |
| 9 | resistor |
| 10 | high-side driver IC |
| 11 | low-side driver IC |
| 12 | fiber optic cable |
| 13 | polarizer optics |
| 14 | polarization cell |
| 15 | He-3 or Xe-129 gas |
| 16 | Helmholtz coils |
| 17 | single driver |
| 18 | nitrogen gas boil-off pipe |
| 19 | liquid nitrogen supply pipe |
| 20 | HTS cables |
| 21 | heat sink |
| 22 | solid-state laser |

Description of Invention

The new feature of this invention is the cryo-cooled diode laser array based on gallium-arsenide compounds (InGaAs, AlGaInAs, AlGaInAsP) which provides the required light power with less diodes, i.e. at lower cost. Another key new feature is the close integration of the cryogenically cooled drive power electronics. A third feature is the integration of this cryo-laser-driver circuit with a liquid nitrogen (LN2) distribution system which may be implemented with a high-temperature superconducting power cable cooled by LN2 [34].

Laser diodes made from other materials such as silicon-carbide or organic materials [19] may also be used in the future. If the required laser power is P at a cost of $C and the cryo-cooling increases the available laser power by a factor N per diode, then the cost reduction is about a factor N and the new cost $(C/N). The improvement factor N must be determined and is in the order of magnitude of 2–20 according to preliminary measurements (depending on current level). The cooling penalty was neglected here. This is permissible since the diodes are very expensive ($400 to $1000/Watt) and liquid nitrogen is relatively cheap. In other words, there are certainly laser applications where the high cost of the laser can be advantageously traded for the low cost of liquid nitrogen, which will be distributed over time anyway. Besides, almost all hospitals and many industrial establishments have liquid oxygen and liquid nitrogen available on site for other purposes. In addition, many also have magnetic resonance imaging machines based on superconductor magnets which provide a cryogenic power base. In addition, one can expect a widespread use of high-temperature superconductor cables for energy distribution in the near future. These cables are cooled by liquid nitrogen and can therefore serve in a dual use function as low-cost LN2 supplies.

The laser diode drivers are also implemented as cryo-circuits using Cryo-MOSFETs which exhibit an order of magnitude lower on-resistance due to the cooling. Cryo-CMOS devices are also used as driver circuits for the cryo-diode lasers.

In summary, the semiconductor Cryo-Diode-Laser (CDL) concept (77K–250K) using commercially available or specifically optimized components as proposed in this invention provides the following features:

Much higher power levels compared to room temperature operation. This means more (light) watts per dollar, more output power in a smaller volume.

Higher conversion efficiency due to cryogenic (77 K–250 K) operation despite the cooling penalty. Result: Energy savings.

Higher reliability and longer lifetimes due to the low temperature operation.

Improved thermal management of the high power densities occurring inside the small semiconductor junctions due to the fact that the thermal conductivity of GaAs and their substrates (beryllium-oxide, etc.) increases by an order of magnitude when cryo-cooled. This translates into more uniform temperature profiles inside the chip and therefore improved optical output patterns. Thermal management is especially important for high-power diode laser arrays and bars.

Many lasers require (pulse) power supplies with high output power levels. A suitable power supply is integrated by applying the new concept of cryogenic power conversion using cryo-MOSFETs and/or Cryo-CMOS devices.

The cooling penalty and cost can be relatively low, especially in pulsed or low-duty cycle applications, i.e. few operating hours per day. One can trade the high-cost for laser diodes for the low-cost of liquid nitrogen. The latter cost is also distributed over time (months and years).

Multi-layer insulation (MLI) can be used to implement an energy storage capacitor for pulsed laser applications.

Figure 7:
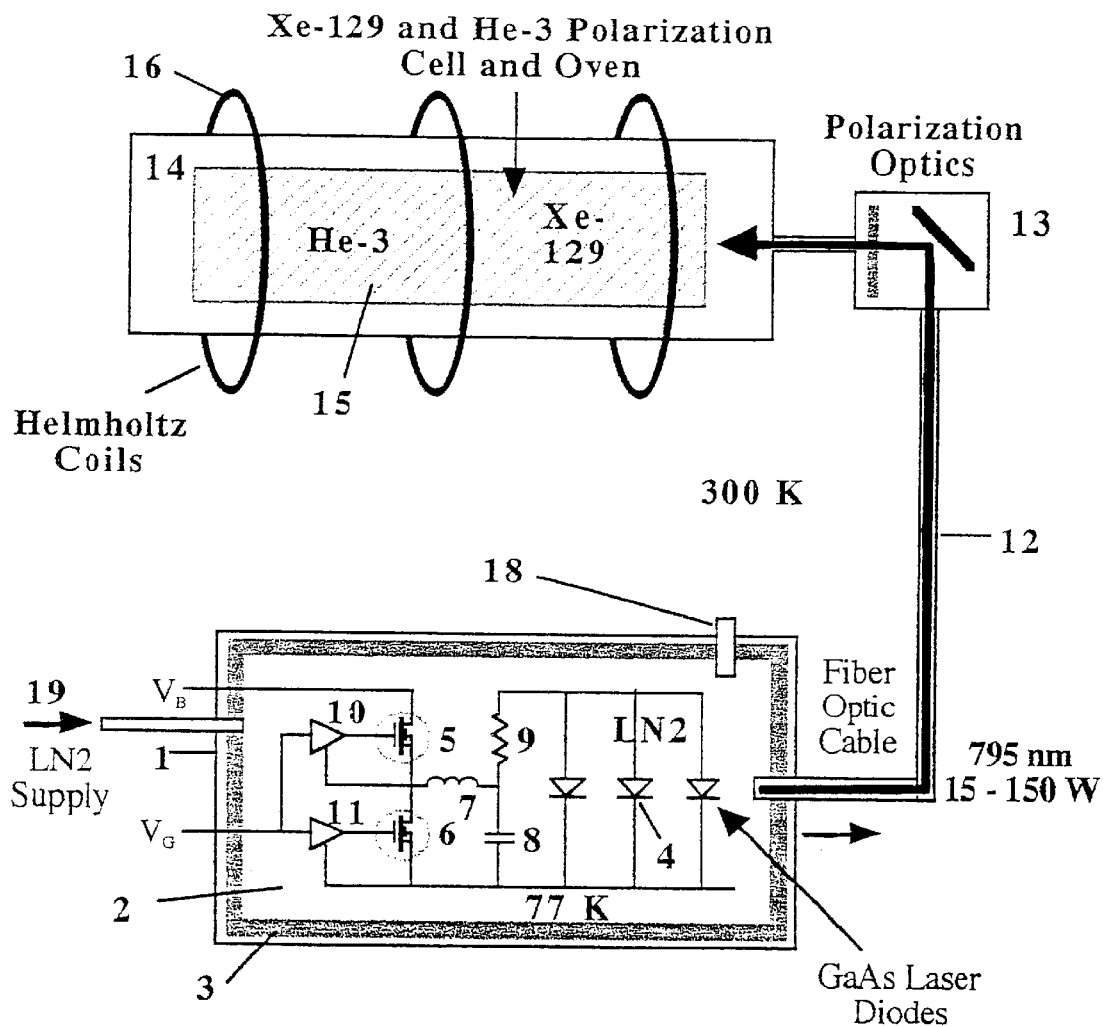
FIG. 7.

The Cryo-Diode Laser assembly of FIG. 7 can, of course, also be used for many other applications besides hyperpolarized gas generation for MRI. An obvious one in a hospital environment is laser surgery [20–22]. The availability of cryogenics is also beneficial to cryo-surgery equipment. Today, lasers are the most effective new materials processing tools [9–26]. For most of the multitude of manufacturing applications high light output power levels are required, especially for:

annealing metals, cutting and drilling, heat treatment, non-destructive testing, printing [12], paint removal, contactless soldering [11], solid preform fabrication (SPF) via metal and ceramic powder sintering [23], surface cladding and treatment, light welding and sealing [15], laser surgery [20–22], diode pumping of solid-state and gas lasers, graphics and pulsed laser deposition [25], laser communication systems, etc.

Due to its higher power capability and lower cost, the cryo-diode laser may be used for most of these applications, even if diode lasers are not yet used in a given field. It should be noted that many of these manufacturing applications require high pulsed-power at low duty cycles. Therefore, the consumption of liquid nitrogen is relatively low. LN2 can be generated at low power consumption times such as during the night or on weekends. Thus the proposed high-power cryo-diode laser system also provides 'load shedding'. This may be important in all applications where very high laser light power levels are required (100 W to kilowatts), for example in industrial laser welding, cutting, etc.

Besides semiconductor lasers (gallium-arsenide compounds: InGaAs, AlGaInAs, AlGaInAsP), four families of lasers are available [26]:

a) dye lasers using liquid organic dyes (pumped), b) gas and metal vapor lasers (argon, argon/krypton, CO2, CO, deuterium-fluoride, helium-cadmium, helium-neon, krypton, copper vapor at high temperatures), c) solid-state lasers: Highest power: Erbium, neodymium:YAG, holmium, neodymium-glass, ruby, Ti:sapphire.

e) organic lasers [19].

The first three types are relatively large, are complicated in their construction, use glass tubes, are inefficient, but are capable of high power outputs. The key features of the semiconductor laser diodes are extreme simplicity, small size, high-efficiency, and high reliability. But their power output is limited by the ability to remove heat from the device. All lasers are still relatively expensive, especially the high powered devices required for the processing of advanced materials such as metals, ceramics, glass, polymer/plastics, composites, etc. Therefore, there is a need for lasers with higher efficiency and higher power at lower cost in order to reduce energy consumption. This need is fulfilled by the Cryo-Diode-Laser discussed here.

The current status is best described by the following statement: "With their compact size, high efficiency, and low cost in mass production, high-power, fiber-coupled, diode laser arrays are a very promising alternative to CO2 and Nd:YAG in laser material processing applications." [6]. This invention will make that statement even more valid.

Cryo-diode lasers (CDL) incorporating Cryo-Drivers may become ubiquitous for many applications mentioned above especially when high-temperature superconductor (HTS) cables now under development by such companies as ASC, Pirelli, IGC, etc. find widespread applications [34]. These cables will deliver not only electrical power but also cooling fluids such as liquid nitrogen (LN2, 77 K). Even higher power levels are required for many materials processing applications, where any size, weight and cost reduction at increased efficiency translates immediately into environmental and economic benefits. Any drastic cost reduction will enable more widespread distribution of laser systems.

References

1. M. S. Albert, G. D. Cates, B. Driehuys, et al: "Biological magnetic resonance imaging using laser-polarized Xe-129". Nature, Vol. 370, Jul. 21, 1994, pp. 199–201.
2. W. J. Cummings, O. Häusser, W. Lorenzen, D. R. Swenson, B. Larson: "Optical pumping of Rb vapor using high-power GaAlAs diode laser arrays". Physical Review A, Vol. 51, No. 6 June 1995, 4842–4851.
3. R. D. Black, et al.: "In Vivo He-3 MR images of Guinea Pigs Lungs." Radiology, Vol. 199, June 1996, pp. 867–870.
4. M. S. Albert: "Airway Disease: Hyperpolarized Gas MRI", Conf. Proc., ISMRM-98, p. 413.
5. S. Rosen, et al.: "Production and Delivery of Polarized X-129 for In-Vivo MRS/MRI". Conf. Proc., ISMRM-98, p. 1911.
6. T. Dearmin: "High-Power Diode Lasers Make Strong Impression in Graphics and Medical Imaging Applications". Opto-Power Corporation website, 7/98.
7. J. MacFall, H. C. Charles, R. D. Black, et al.: "Human Lung Air Spaces: Potential for MR Imaging with Hyperpolarized He-3". Radiology, Vol. 200, No. 2, August 1996, 553–558.
8. G. A. Johnson, et al.: "Inert Gas Imaging". Center for In Vivo Microscopy, Duke University, NC, Website, 7/98.
9. T. Chupp: "Opto Power OEM Laser Modules Have Made a Host of Exciting New Experiments Feasible and Practical". Opto Power Corporation Website, 7/98.
10. J. Tracy: "Diode Lasers Find a Role in Direct Thermal Apps". Photonics Spectra, January 1996.
11. C. Roychoudhuri: "Opto Power Diode Laser Arrays are Helping Make Laser Material Processing a Reality." Opto Power Corporation, Article, (http://www.optopower.com/opc/test1.htm)
12. C. Frederickson, "Gas, Solid-State Lasers Battle for Printers' Best Impressions: Developments in printing plate materials increase printers' appetites for diode and diode-pumped solid-state lasers," *Photonics Spectra*, October 1997, pp. 138–140
13. J. Hecht, "Lasers in Industrial Applications," *Laser Focus World*, April 1994, pp. 67–70
14. R. Mendonsa, "Laser Helps Make Short Work of 3-D Model Making," *Photonics Spectra*, September 1997, p. 128
15. D. Havrilla and T. Webber, "Laser Welding Takes the Lead," *Lasers & Optronics*, March 1991, pp. 30–40
16. D. Morrison, "Lasers—The Lightning of Desert Storm," *Lasers & Optronics*, March 1991, pp. 43–46
17. S. McCall and N. Dutta, "Diode Lasers Invigorate Communication Technologies: Semiconductor-laser devices grow smaller and easier to integrate without sacrificing power and versatility for high performance in tele- and data-communications systems," *Laser Focus World*, October 1992, pp. 7583.
18. News: "Solid-State Diode Lasers Gain Ground", *Photonics Spectra*, December 1997, p. 42.
19. A. W. Hardin: "Princeton Promises Much on Organic Lasers", *Photonics Spectra*, December 1997, p. 34.
20. T. E. Bell: Innovations: "GaAs versus Gas Lasers for Surgery." IEEE Spectrum, February 1997, p. 16.
21. J. Marciante and G. Agrawal, "Nonlinear Mechanism of Filamentation in Broad-Area Semiconductor Lasers," *IEEE Journal of Quantum Electronics*, Vol. 32, No. 4, April 1996, pp. 590–596
22. J. Marciante and G. Agrawal, "Controlling Filamentation in Broad-Area Semiconductor Lasers and Amplifiers," *Applied Physics Letters*, Vol. 69, No. 5, July 1996, pp. 593–595
23. S. C. Hennink, "Machining Lasers Find Niches by Solving Very Small Problems: Applications include cutting curves, drilling tiny holes and creating microwelds". *Photonics Spectra*, November 1997, pp. 116–118.
24. M. A. Marinelli, J. T. Remillard: "Diode Lasers Light the Way for Automotive Signal Lamps". *Photonics Spectra*, November 1997, pp. 110–114.
25. Neocera Ad: "Pulsed Laser Deposition". Superconductor Industry, Fall 1997, p. 3.
26. Laser Focus World: The Buyers Guide 1994.
27. O. Mueller, "Cryo-MOSFET and IGBT: A comparison", Second European Workshop on Low Temperature Electronics (WOLTE-2), Journal de Physique, colloque 3, vol. 6, pp. C3.219–C3.224, Leuven, Belgium, June 1996.
28. O. Mueller, "Properties of high-power cryo-MOSFETs," Conference Record of the 1996 Annual IEEE Industrial Applications Society Meeting (IAS-96), vol. 3, pp. 1443–1448 (IEEE 96CH35977), San Diego, Calif., October 1996.
29. O. Mueller, W. A. Edelstein, and P. B. Roemer, "The cryogenic NMR gradient amplifier," Eighth Annual Meeting, Society of Magnetic Resonance in Medicine, Book of Abstracts, Part 2, p. 970, Amsterdam, The Netherlands, Aug. 12–18, 1989
30. O. Mueller, "On-resistance, thermal resistance, and reverse recovery time of power MOSFETs at 77 K," Cryogenics, vol. 29, pp. 1006–1014, October 1989
31. O. Mueller, "Cryogenic MOSFET power conversion," Proceedings of the IEEE Workshop on Low Temperature Semiconductor Electronics, pp. 94–98, University of Vermont, Aug. 7 & 8, 1989 (IEEE 89TH0252-7)
32. E. Mueller, O. Mueller: "High-speed cryo-CMOS driver circuits for power inverters". CEC-ICMC-99, Montreal, July 1999. Conference Paper CEC-1.
33. O. Mueller, E. Mueller: "Cryogenic power inverters for magnetic resonance imaging (MRI) systems". CEC-ICMC-99, Monteral, Jul. 12–16, 1999. Conference Paper CEC-2.
34. O. Mueller, E. Mueller: "Cryogenic power/energy distribution system". CEC-ICMC-99, Montreal, July 1999. Conference Paper CPC-1.

Trademarks

It is planned to file for LTE-trademark protection for the following terms:

Cryo-Laser™, Cryo-Diode-laser™, Cryo-Light™, CDL™.

What is claimed is:
1. A photon emitter comprising:

a semiconductor laser active medium having an enhanced laser output when said laser is operated at a reduced temperature below 300K;

a refrigeration means in a heat transfer relationship with said semiconductor laser medium to maintain said laser at said reduced temperature with enhanced performance, heat produced by said laser operation when said laser is pumped is transferred to said refrigeration means to thereby enhance photon emission.

2. A photon emitter as in claim 1, wherein said enhancement occurs at a cryogenic temperature provided by said refrigeration means.

3. A photon emitter as in claim 1, further comprising a semiconductor driver circuit connected to and in operation driving said laser, said semiconductor driver circuit being cooled to a reduced temperature by said refrigeration means, said semiconductor driver circuit having enhanced performance at said reduced temperature.

4. A photon emitter as in claim 3, further comprising a power supply and a control signal generator connected to and in operation energizing said driver circuit.

5. A photon emitter as in claim 3, further comprising a thermally insulated container enclosing said laser and driver circuit.

6. A photon emitter as in claim 4, further comprising a thermally insulated container enclosing said laser and driver circuit.

7. A photon emitter as in claim 6, further comprising radiation transmission means for receiving in said insulated container radiation output of said laser and delivering said radiation output outside said container.

8. A photon emitter as in claim 7, further comprising radiation transmission means for receiving in said insulated container radiation output of said laser and delivering said radiation output outside said container.

9. A photon emitter as in claim 6, wherein said refrigeration means includes one of a liquid and gaseous refrigerant, said laser and driver circuit respectively being one of submerged for cooling in said refrigerant and mounted for heat exchange on a heat conductor that is cooled by said refrigerant.

10. A photon emitter as in claim 9, wherein said container includes a vapor vent for release of heated refrigerant.

11. A photon emitter as in claim 10, wherein said liquid cryogenic refrigerant is one of nitrogen and helium, and said gaseous refrigerant is one of nitrogen, mixed-gas refrigerants, and gas derived from heated salid material.

12. A photon emitter as in claim 6, wherein said radiation transmission means includes at least one of fiber optic cables, optical wave guides, and light pipes transmitting radiation from said laser.

13. A photon emitter as in claim 6, wherein said semiconductor driver circuit includes at least one of cryo-MOSFETS and cryo-CMOS integrated circuits having enhanced performance at cryogenic temperatures.

14. A photon emitter as in claim 13, wherein said semiconductor driver circuit is integrated with an alternating current to direct current converter, said converter including at least one of cryo-MOSFETS and cryo-CMOS integrated circuits having enhanced performance at cryogenic temperatures.

15. A photon emitter as in claim 14, wherein said semiconductor driver circuit is integrated with an direct current to direct current converter, said converter including at least one of cryo-MOSFETS and cryo-CMOS integrated circuits having enhanced performance at cryogenic temperatures.

16. A photon emitter as in claim 4, wherein said driver circuit includes integrated circuits, said integrated circuits being mounted on a heat conductor for efficient removal of heat from said integrated circuits by said refrigeration means.

17. A photon emitter as in claim 4, wherein said semiconductor driver circuit includes at least one of cryo-MOSFETS and cryo-CMOS integrated circuits having enhanced performance at cryogenic temperatures.

18. A photon emitter as in claim 18, wherein said semiconductor driver circuit is integrated with a power converter, said converter including at least one of cryo-MOSFETS and cryo-CMOS integrated circuits, said converter integrated circuits providing one of alternating current to direct current conversion and direct current to direct current conversion, and having enhanced performance at cryogenic temperatures.

* * * * *

UNITED STATES PATENT AND TRADEMARK OFFICE
CERTIFICATE OF CORRECTION

PATENT NO. : 6,611,540 B1 Page 1 of 1
DATED : August 26, 2003
INVENTOR(S) : Otward Maria Mueller It is certified that error appears in the above-identified patent and that said Letters Patent is hereby corrected as shown below:

Column 8,
Lines 30, 38, 50 and 54, change "6" to -- 5 --.
Line 34, change "7" to -- 6 --.
Line 46, change "10" to -- 9 --.

Column 9,
Line 1, change "14" to -- 13 --.
Lines 6 and 11, change "4" to -- 3 --.

Column 10,
Line 3, change "claim 18" to -- claim 17 --.
Line 11, add:
    19. A photon emitter as in claim 1, wherein said laser capability enhancement includes at least one of increased radiation power output relative to power input, reduced power input relative to radiation power output, reduced size, and extended life.

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,611,540 B1                                                        Page 1 of 1
DATED          : August 26, 2003
INVENTOR(S)    : Otward Maria Mueller It is certified that error appears in the above-identified patent and that said Letters Patent is hereby corrected as shown below:

Column 8,
Lines 32, 41, 53 and 57, change "6" to -- 5 --.
Line 34, change "7" to -- 6 --.
Line 46, change "10" to -- 9 --.

Column 9,
Line 1, change "14" to -- 13 --.
Lines 6 and 11, change "4" to -- 3 --.

Column 10,
Line 3, change "claim 18" to -- claim 17 --.
Line 11, add:
    19. A photon emitter as in claim 1, wherein said laser capability enhancement includes at least one of increased radiation power output relative to power input, reduced power input relative to radiation power output, reduced size, and extended life.

This certificate supersedes Certificate of Correction issued October 14, 2003

Signed and Sealed this

Eighteenth Day of November, 2003

JAMES E. ROGAN
*Director of the United States Patent and Trademark Office*